US012629137B2

(12) United States Patent
Kim et al.

(10) Patent No.:  US 12,629,137 B2
(45) Date of Patent:  May 19, 2026

(54) ULTRASOUND DIAGNOSTIC APPARATUS AND CONTROL METHOD THEREOF

(71) Applicant: SAMSUNG MEDISON CO., LTD., Hongcheon-gun (KR)

(72) Inventors: Sungho Kim, Seoul (KR); Seoksoon Noh, Paju-si (KR); Donghyun Oh, Hanam-si (KR); Kyungmin Lee, Hanam-si (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 148 days.

(21) Appl. No.: 18/235,532

(22) Filed: Aug. 18, 2023

(65) Prior Publication Data

US 2024/0115241 A1      Apr. 11, 2024

(30) Foreign Application Priority Data

Oct. 7, 2022    (KR) ........................ 10-2022-0129085

(51) Int. Cl.
*A61B 8/00*        (2006.01)
*A61B 8/08*        (2006.01)

(52) U.S. Cl.
CPC .......... *A61B 8/5207* (2013.01); *A61B 8/4477* (2013.01)

(58) Field of Classification Search
CPC ... A61B 8/5207; A61B 8/4477; A61B 8/5269; A61B 8/58; A61B 8/54; G01S 15/8915; G01S 7/5205
See application file for complete search history.

(56) References Cited

U.S. PATENT DOCUMENTS

| | | | | |
|---|---|---|---|---|
| 5,697,372 A | * | 12/1997 | Hughes ................. | G01S 7/5205 600/444 |
| 2013/0303907 A1 | * | 11/2013 | Corl ....................... | A61B 8/488 600/443 |
| 2017/0153322 A1 | | 6/2017 | Hayashi | |
| 2021/0353258 A1 | | 11/2021 | Tezuka et al. | |

FOREIGN PATENT DOCUMENTS

| | | |
|---|---|---|
| EP | 0713102 A1 | 5/1996 |
| JP | H106-43237 A | 2/1994 |
| JP | 2011-005023 A | 1/2011 |
| JP | 2011-005024 A | 1/2011 |
| JP | 2011-072701 A | 4/2011 |
| JP | 2012-139460 A | 7/2012 |
| JP | 2014-064852 A | 4/2014 |

(Continued)

OTHER PUBLICATIONS

Extended European Search Report issued Jan. 23, 2024 for European Patent Application No. 23190819.5.

(Continued)

*Primary Examiner* — Amal Aly Farag
(74) *Attorney, Agent, or Firm* — Morgan Lewis & Bockius LLP

(57)        ABSTRACT

An ultrasonic diagnostic apparatus includes a probe including a plurality of elements provided to transmit an ultrasonic signal to an object and receive an echo signal reflected from the object, and a processor modifying the echo signal based on comparing frequency characteristic data of the echo signal with pre-stored normal frequency characteristic data and amplifying the modified echo signal.

12 Claims, 14 Drawing Sheets

(56) References Cited

FOREIGN PATENT DOCUMENTS

| | | |
|---|---|---|
| JP | 2017-93869 A | 6/2017 |
| KR | 10-0948048 B1 | 3/2010 |
| WO | 2019/081269 A1 | 5/2019 |

OTHER PUBLICATIONS

European Communication dated Nov. 4, 2025 issued in European Patent Application No. 23190819.5.
European Communication dated Jan. 15, 2026 issued in European Patent Application No. 23190819.5.

* cited by examiner (a)

FIG. 8

ULTRASOUND DIAGNOSTIC APPARATUS AND CONTROL METHOD THEREOF

CROSS-REFERENCE TO RELATED APPLICATION(S)

This application is based on and claims priority under 35 U.S.C. § 119 to Korean Patent Application No. 10-2022-0129085, filed on Oct. 7, 2022, in the Korean Intellectual Property Office, the disclosure of which is incorporated by reference herein in its entirety.

BACKGROUND

1. Field

The disclosure relates to an ultrasonic diagnostic apparatus receiving an ultrasonic image from a probe and a control method thereof.

2. Description of the Related Art

An ultrasonic diagnostic apparatus is a device that obtains an image of a target part in a body of an object by radiating an ultrasonic signal generated from a transducer of an ultrasonic probe from a body surface of the object toward the target part in the body and receiving information of the ultrasonic signal (ultrasonic echo signal) reflected from the object.

The ultrasonic diagnostic apparatus is widely used in the field of medical diagnosis because it is more stable than an X-ray imaging apparatus because there is no exposure to radiation, etc., may display images in real time, is cheaper than a magnetic resonance imaging apparatus, and is portable.

On the other hand, the performance of the ultrasonic probe may degrade for various reasons during use, and in particular, when an element provided in the ultrasonic probe is degradative, the quality of an ultrasonic image may be degraded. Therefore, when a technology for compensating for the degradation of an element is applied to the ultrasonic diagnostic apparatus, the quality of the ultrasonic image may be maintained.

SUMMARY

It is an aspect of the disclosure to provide an ultrasonic diagnostic apparatus capable of compensating an ultrasonic signal based on a degree of degradation of an element and a control method thereof.

Additional aspects of the disclosure will be set forth in part in the description which follows and, in part, will be obvious from the description, or may be learned by practice of the disclosure.

In accordance with an aspect of the disclosure, an ultrasonic diagnostic apparatus includes a probe including a plurality of elements provided to transmit an ultrasonic signal to an object and receive an echo signal reflected from the object, and at least one processor configured to modulate the echo signal based on comparing frequency characteristic data of the echo signal with pre-stored normal frequency characteristic data and amplify the modulated echo signal.

The at least one processor may modulate the echo signal based on comparing the same frequency bands of the frequency characteristic data of the echo signal and the normal frequency characteristic data.

The at least one processor may determine a frequency band having a maximum difference in amplitudes in the same frequency band, and modulate the echo signal based on the frequency band in which the difference in the amplitudes is maximum.

The at least one processor may modulate the echo signal by applying frequency filters so that the difference in the amplitudes in the same frequency band is equal to the difference in the amplitudes in the frequency band in which the difference in the amplitudes is maximum.

The at least one processor may amplify the modulated echo signal so that the difference in the amplitudes of the frequency characteristic data of the modulated echo signal and the normal frequency characteristic data in the same frequency band decreases to a preset threshold value or less.

The at least one processor may modulate the echo signal by selecting one of the frequency filters stored in the form of a look-up table.

The normal frequency characteristic data may include normal pulse echo data of the elements.

The at least one processor may modulate the echo signal by comparing pulse echo data obtained through the plurality of elements with the normal pulse echo data.

The at least one processor may modulate the echo signal by comparing in-air image data obtained through the plurality of elements with the normal pulse echo data.

The at least one processor may obtain element inspection data based on receiving a user input for inspecting the plurality of elements, and modulate the echo signal by comparing the element inspection data with the normal pulse echo data.

In accordance with another aspect of the disclosure, a control method of an ultrasonic diagnostic apparatus includes a plurality of elements provided to transmit an ultrasonic signal to an object and receive an echo signal reflected from the object and a probe, wherein the control method includes modulating the echo signal based on comparing frequency characteristic data of the echo signal with pre-stored normal frequency characteristic data, and amplifying the modulated echo signal.

The modulating of the echo signal may include modulating the echo signal based on comparing the same frequency bands of the frequency characteristic data of the echo signal and the normal frequency characteristic data.

The modulating of the echo signal may include determining a frequency band having a maximum difference in amplitudes in the same frequency band, and modulating the echo signal based on the frequency band in which the difference in the amplitudes is maximum.

The modulating of the echo signal may include modulating the echo signal by applying frequency filters so that the difference in the amplitudes in the same frequency band is equal to the difference in the amplitudes in the frequency band in which the difference in the amplitudes is maximum.

The modulating of the echo signal may include amplifying the modulated echo signal so that the difference in the amplitudes of the frequency characteristic data of the modulated echo signal and the normal frequency characteristic data in the same frequency band decreases to a preset threshold value or less.

The modulating of the echo signal may include modulating the echo signal by selecting one of the frequency filters stored in the form of a look-up table.

The normal frequency characteristic data may include normal pulse echo data of the elements.

The modulating of the echo signal may include modulating the echo signal by comparing pulse echo data obtained through the plurality of elements with the normal pulse echo data.

The modulating of the echo signal may include modulating the echo signal by comparing in-air image data obtained through the plurality of elements with the normal pulse echo data.

The modulating of the echo signal may include obtaining element inspection data based on receiving a user input for inspecting the plurality of elements, and modulating the echo signal by comparing the element inspection data with the normal pulse echo data.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 8 is a control block diagram of the ultrasonic diagnostic apparatus according to an embodiment;

DETAILED DESCRIPTION

Figure 1:
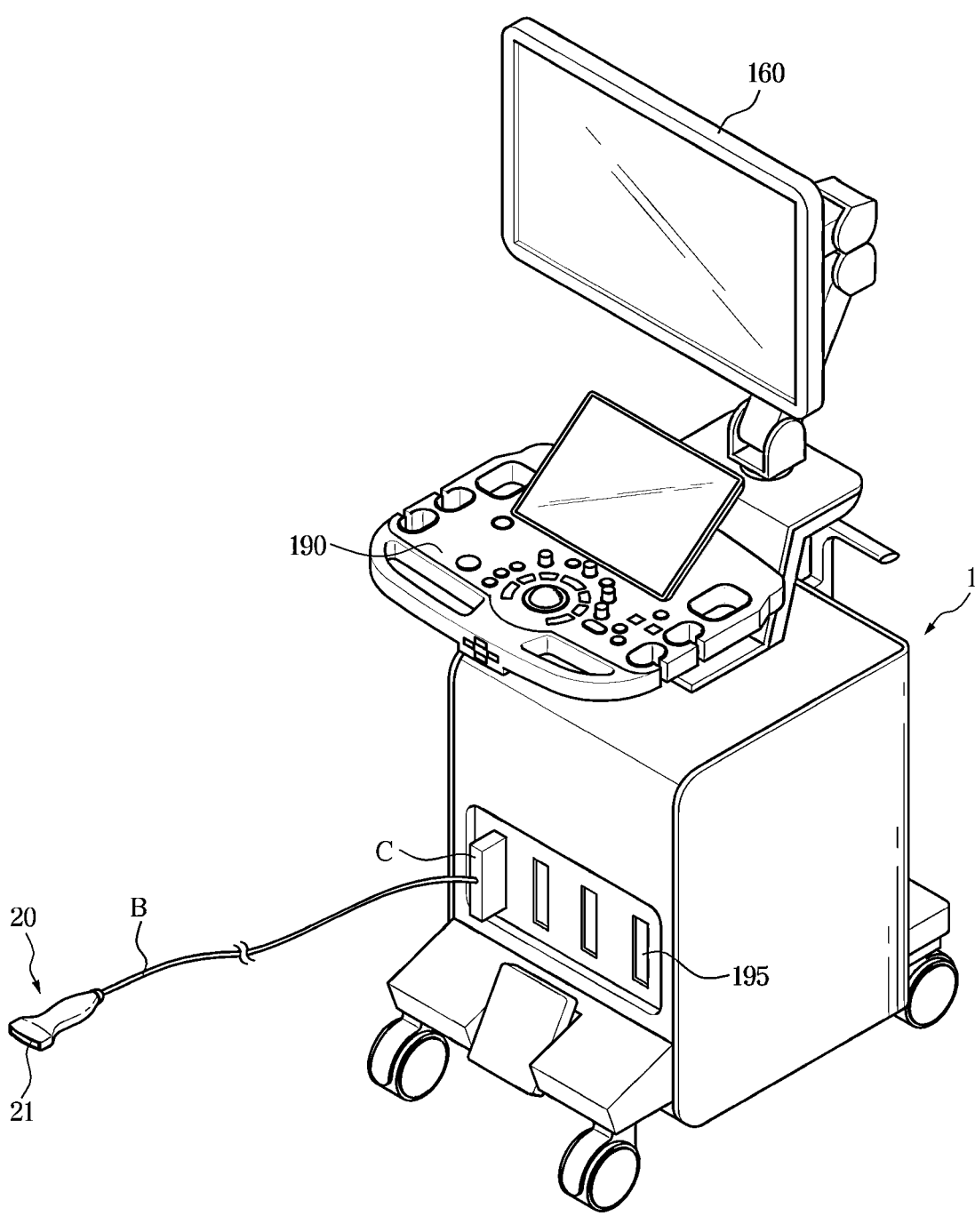
FIG. 1 is an external perspective view of an ultrasonic diagnostic apparatus according to an embodiment.

Throughout the specification, like reference numerals refer to like elements. This specification does not describe all the elements of the embodiments, and general contents or duplicative contents between embodiments in the technical field of the disclosure will be omitted. The terms 'unit,' 'module,' 'member,' and 'block' used in this specification may be embodied as software or hardware, and it is also possible for a plurality of 'units,' 'modules,' 'members,' and 'blocks' to be embodied as one component, or one 'unit,' 'module,' 'member,' and 'block' to include a plurality of components according to embodiments.

Throughout the specification, when a part is referred to as being "connected" to another part, it includes not only a direct connection but also an indirect connection, and the indirect connection includes connecting through a wireless network.

Also, when it is described that a part "includes" an element, it means that the element may further include other elements, not excluding the other elements unless specifically stated otherwise.

Throughout the specification, when a component is described as being located "on" or "over" another component, this includes not only a case in which a component is in contact with another component but also a case in which another component is present between the two components.

The terms 'first,' 'second,' etc. are used to distinguish one component from another component, and the components are not limited by the above-mentioned terms.

The singular forms "a" "an," and "the" include plural referents unless the context clearly dictates otherwise.

In each step, an identification numeral is used for convenience of explanation, the identification numeral does not describe the order of the steps, and each step may be performed differently from the order specified unless the context clearly states a particular order.

Hereinafter, an operation principle and embodiments of the disclosure will be described with reference to the accompanying drawings.

FIG. 1 is an external perspective view of an ultrasonic diagnostic apparatus 1 according to an embodiment.

Referring to FIG. 1, the ultrasonic diagnostic apparatus 1 may be connected to a probe 20 provided to transmit an ultrasonic signal to an object and receive an echo ultrasonic signal from the object to convert the received echo ultrasonic signal into an electrical signal.

The ultrasonic diagnostic apparatus 1 may be connected to the probe 20 through a wired communication network or a wireless communication network. The ultrasonic diagnostic apparatus 1 may be a workstation having a display unit 160 and an input device 190. In addition, the ultrasonic diagnostic apparatus 1 may exchange a variety of information with an external device through a wired communication network or a wireless communication network.

The input device 190 may receive various control commands, such as an operation for the connected probe 20 and an operation command for the ultrasonic diagnostic apparatus 1 generating an ultrasonic image. The input device 190 may be implemented as various hardware devices such as a keyboard, a foot switch, and a foot pedal. For example, when the input device 190 is implemented as the keyboard, the keyboard may include at least one of a switch, a key, a joystick, and a trackball. As another example, the keyboard may be implemented as software, such as a graphical user interface. In this case, the keyboard may be displayed through a second display. The foot switch or foot pedal may be provided at a lower portion of the ultrasonic diagnostic apparatus 1, and a user may control an operation of the ultrasonic diagnostic apparatus 1 by using the foot pedal.

An ultrasonic image generated by the ultrasonic diagnostic apparatus 1 and various graphic user interfaces may be displayed on the display unit 160.

The display unit 160 may include, for example, a first display and the second display.

An ultrasonic image displayed on the first display may be a two-dimensional ultrasonic image or a three-dimensional ultrasonic image, and various ultrasonic images may be displayed on the first display according to an operating mode of the ultrasonic diagnostic apparatus 1. In addition, the first display may display information on an operating state of the probe 20, as well as menus or guidance notes necessary for ultrasonic diagnosis.

The second display may provide a menu for optimizing an ultrasonic image or information related to an auxiliary image, or provide a graphic user interface to the user. When the second display serves as the input device 190, a graphic user interface having the same shape as a button included in the input device 190 may be displayed on the second display.

The form of the ultrasonic diagnostic apparatus 1 is not necessarily limited to that illustrated in FIG. 1. For example, the ultrasonic diagnostic apparatus 1 may be implemented in the form of a smart phone as well as a laptop, desktop, and tablet PC. The ultrasonic diagnostic apparatus 1 may also be implemented in the form of a mobile terminal such as a personal digital assistant (PDA), a watch attachable to and detachable from a body of the user, and a wearable terminal in the form of eyeglasses.

The object may be a living body of a human or animal, or a tissue in vivo such as blood vessels, bones, and muscles, but is not limited thereto, and it may become the object as long as its internal structure may be imaged by ultrasonic diagnostic apparatus 1.

The probe 20 may include a transducer provided in a housing to irradiate ultrasonic waves to the object, receive echo ultrasonic wave reflected from the object, and mutually convert an electrical pulse signal and an ultrasonic wave, a male connector C physically coupled to a female connector 195 of the ultrasonic diagnostic apparatus 1 to transmit and receive signals to and from the ultrasonic diagnostic apparatus 1, and a cable B provided to connect the ultrasonic diagnostic apparatus 1 and the probe 20.

The transducer may generate ultrasonic waves depending on an applied AC power source. Specifically, the transducer may receive AC power from a power storage device inside the probe 20, for example, a battery. A vibrator (hereinafter referred to as a transducer element) 21 of the transducer may generate ultrasonic waves by vibrating depending on the supplied AC power.

The transducer also receives a signal reflected from the object, that is, the echo ultrasonic wave. The transducer converts the echo ultrasonic wave into the electrical signal. The echo ultrasonic waves have various frequency bands or energy intensities for generating various ultrasonic images depending on diagnosis modes.

The probe 20 transmits an analog signal or a digital signal of ultrasonic waves converted by each of the transducer elements 21 to the ultrasonic diagnostic apparatus 1 through the cable B. The disclosed probe 20 is not necessarily connected to the ultrasonic diagnostic apparatus 1 through the cable B. The probe 20 and the ultrasonic diagnostic apparatus 1 may transmit and receive signals through wired or wireless communication.

The ultrasonic diagnostic apparatus 1 includes a probe select assembly (PSA) board provided to receive a signal transmitted by the probe 20. The PSA board may include a plurality of the female connectors 195 to which a plurality of the probes 20 may be connected, and may include a switcher and a plurality of channel unit therein. The PSA board transfers the received signal to a reception delay unit. A detailed description of the ultrasonic diagnostic apparatus 1 will be described below through other drawings.

Figure 2:
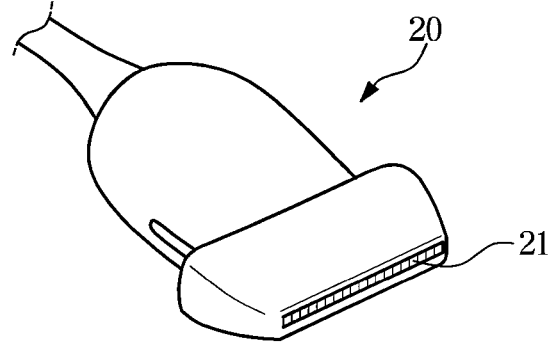
FIG. 2 is an external view of a probe including a one-dimensional array of transducer elements.
Figure 3:
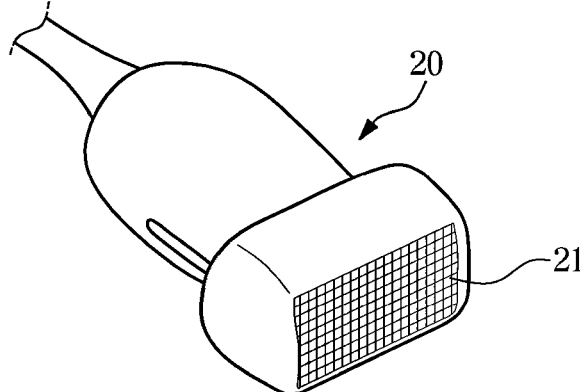
FIG. 3 is an external view of the probe including a two-dimensional array of the transducer elements.

FIG. 2 is an external view of a probe including a one-dimensional array of the transducer elements 21. Also, FIG. 3 is an external view of the probe including a two-dimensional array of the transducer elements 21. In order to avoid overlapping descriptions, the drawings will be described together below.

As described above with reference to FIG. 1, the probe 20 converts the pulse signal received from a main body into an ultrasonic signal, transmits the ultrasonic signal to a specific part inside the object, receives an echo ultrasonic signal reflected from the specific part inside the object, converts the echo ultrasonic signal back into a pulse signal, and transmits the pulse signal to the ultrasonic diagnostic apparatus 1.

The probe 20 may include the transducer element 21 provided to mutually convert an electrical pulse signal and an ultrasonic signal in order to transmit an ultrasonic signal inside the object. A transducer array consists of single or a plurality of the transducer elements 21.

The transducer array may be a one-dimensional array or a two-dimensional array. As an example, the transducer may include the one-dimensional transducer array as illustrated in FIG. 2.

Each of the transducer elements 21 constituting the one-dimensional transducer array may mutually convert an ultrasonic signal and an electrical signal. To this end, the transducer element 21 may be implemented as a magnetostrictive ultrasonic transducer using the magnetostrictive effect of a magnetic material, a piezoelectric ultrasonic transducer using the piezoelectric effect of a material, or a piezoelectric micromachined ultrasonic transducer (pMUT), and may also be implemented as a capacitive micromachined ultrasonic transducer (hereinafter abbreviated as cMUT) that transmits and receives ultrasonic waves using vibrations of hundreds or thousands of micromachined thin films.

The one-dimensional array may be arranged linearly or may be arranged in a convex surface as illustrated in FIG. 2. A basic operating principle of the probe 20 is the same in both cases, but in the case of the probe 20 in which the transducer array is arranged in the convex surface, because the ultrasonic signal irradiated from the transducer is fan-shaped, the generated ultrasonic image may also be fan-shaped.

As another example, the transducer may include the two-dimensional transducer array as illustrated in FIG. 3. When the transducer includes the two-dimensional transducer array, the inside of the object may be imaged in three dimension. In addition, even when the transducer array of the probe 20 is arranged in one dimension, the probe 20 may transmit an echo ultrasonic signal capable of generating a three-dimensional ultrasonic image to the ultrasonic diagnostic apparatus 1 by obtaining information on a volume inside the object while mechanically moving the one-dimensional transducer array.

Each of the transducer elements 21 constituting the two-dimensional transducer array may be the same as each of the transducer elements 21 constituting the one-dimensional transducer array.

In this case, the transducer element 21 may be degradative by a physical impact in a process of using the ultrasonic diagnostic apparatus 1 or may be degradative by temperature and humidity over time. When the transducer element 21 is degradative in this way, a sensitivity of the ultrasonic probe 20 is affected, and thus the quality including the definition of the ultrasonic image may be degradative.

Figure 4:
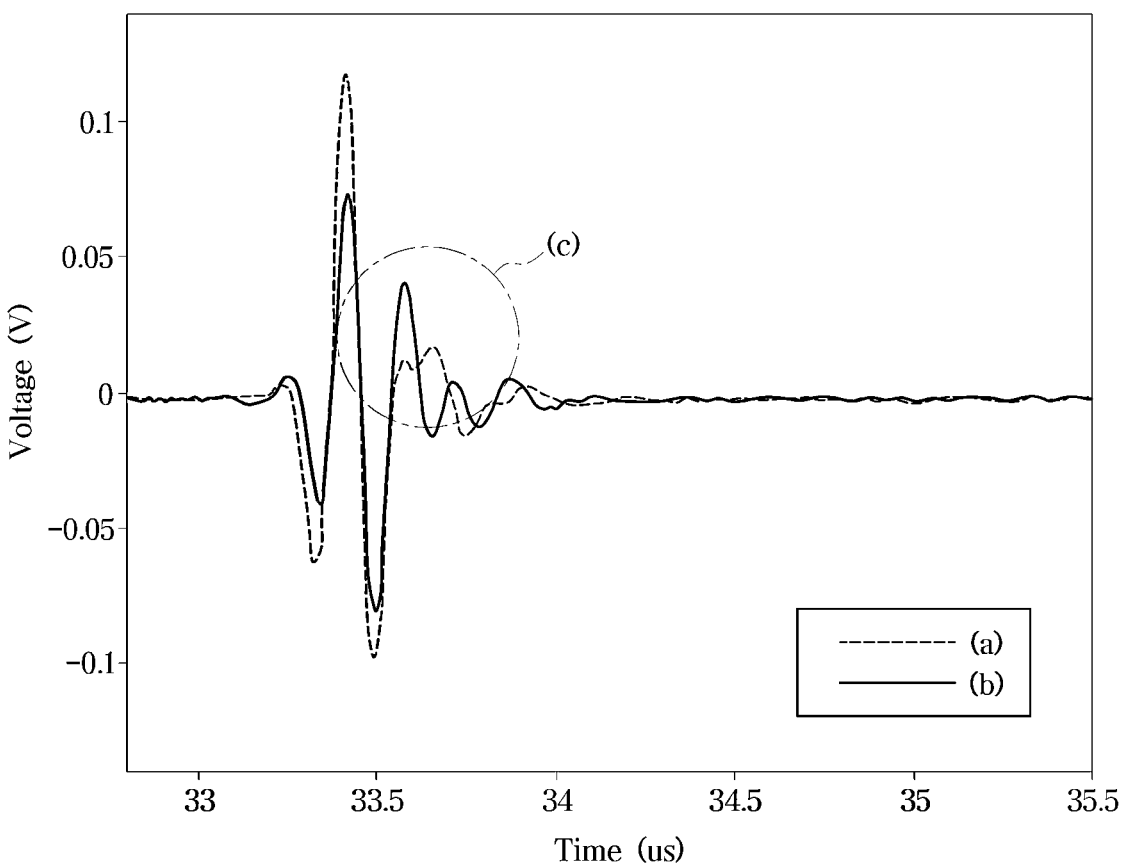
FIG. 4 is a graph related to pulse echo waveforms before and after degradation of the element according to an embodiment.

FIG. 4 is a graph related to pulse echo waveforms before and after degradation of the element according to an embodiment.

Referring to FIG. 4, in the ultrasonic probe 20, a pulse echo waveform may vary before and after degradation of the element 21. Specifically, a pulse echo may refer to data obtained in a process of executing an ultrasonic test to test the performance of the probe 20, and for example, the pulse echo may refer to data obtained by putting the probe 20 in a liquid in a manufacturing plant where the probe 20 is manufactured and transmitting/receiving ultrasonic waves.

In FIG. 4, a waveform (a) of the element 21 before degradation and a waveform (b) of the element 21 after degradation may show a large difference in a specific region (c). For example, in the specific region (c), a section in which valleys and peaks of the waveform (a) before degradation and the waveform (b) after degradation are reversed may occur, which may affect the quality of an ultrasonic image.

In addition, in the waveform (a) before the degradation of the element 21, a Vpp (Vpeak to peak, difference between the maximum voltage and the minimum voltage) voltage may be measured as 0.216 V, and in the waveform (b) after the degradation of the element 21, the Vpp voltage may be measured as 0.154 V.

As such, the degradation of the element 21 may affect the pulse echo waveform of the element 21 to cause degradation of ultrasonic image quality.

Figure 5:
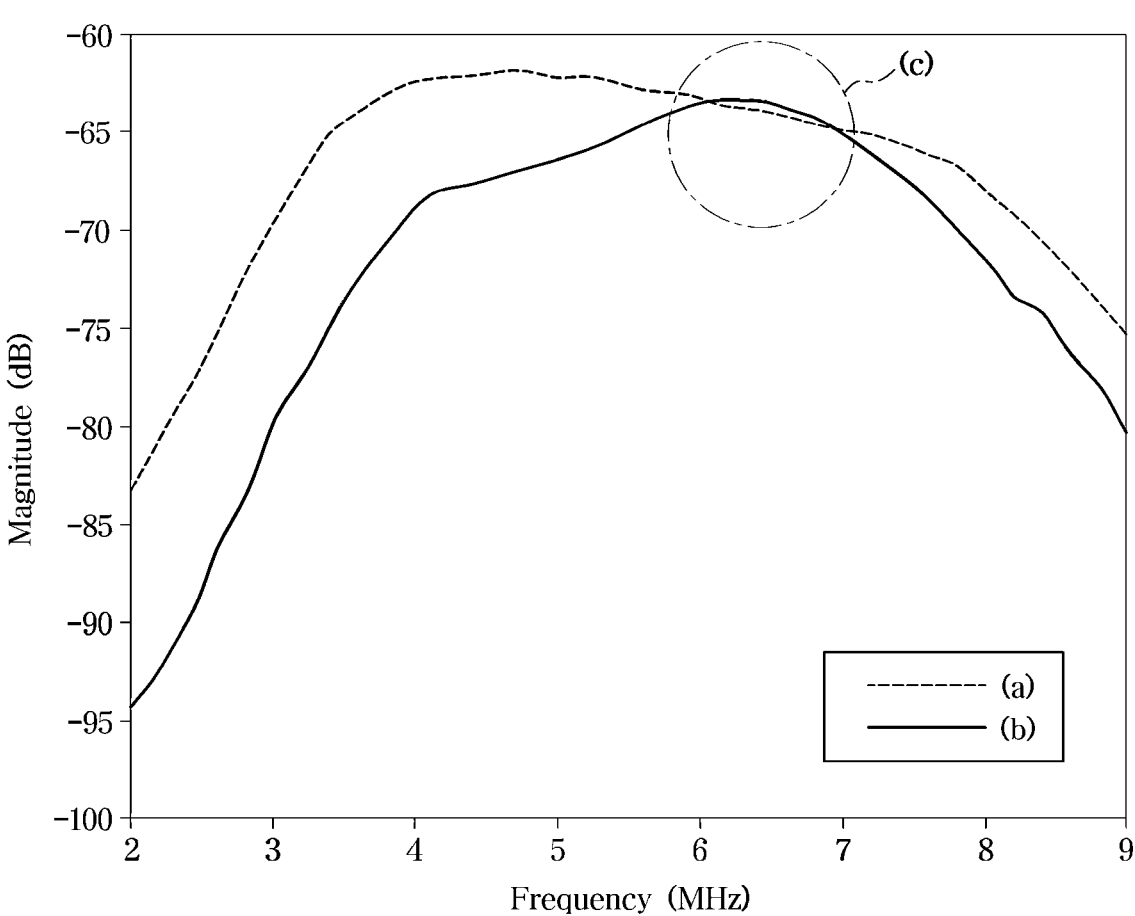
FIG. 5 is a graph related to spectrums before and after the degradation of the element according to an embodiment.

FIG. 5 is a graph related to spectrums before and after the degradation of the element according to an embodiment.

Referring to FIG. 5, in the ultrasonic probe 20, a spectrum of each frequency band of the element 21 may vary before and after the degradation of the element 21. Specifically, an amplitude of each frequency band of the element 21 may vary before and after the degradation of the element 21, and because degrees of degradation of the plurality of elements 21 are different, frequency characteristics before degradation and frequency characteristics after degradation may vary.

In FIG. 5, an amplitude (a) before the degradation of the element 21 and an amplitude (b) after the degradation of the element 21 may show the smallest difference in a specific region (c). For example, in the specific region (c), the amplitude before degradation and the amplitude after degradation may be the same, or a difference in the amplitudes may be less than 1 dB.

However, in regions other than the specific region (c), a difference in amplitudes of 5 dB to 10 dB may occur, which may affect the quality of an ultrasonic image.

As a result, the degradation of the element 21 may affect the amplitude of each frequency of the element 21 to cause degradation of the ultrasonic image quality.

Figure 6:
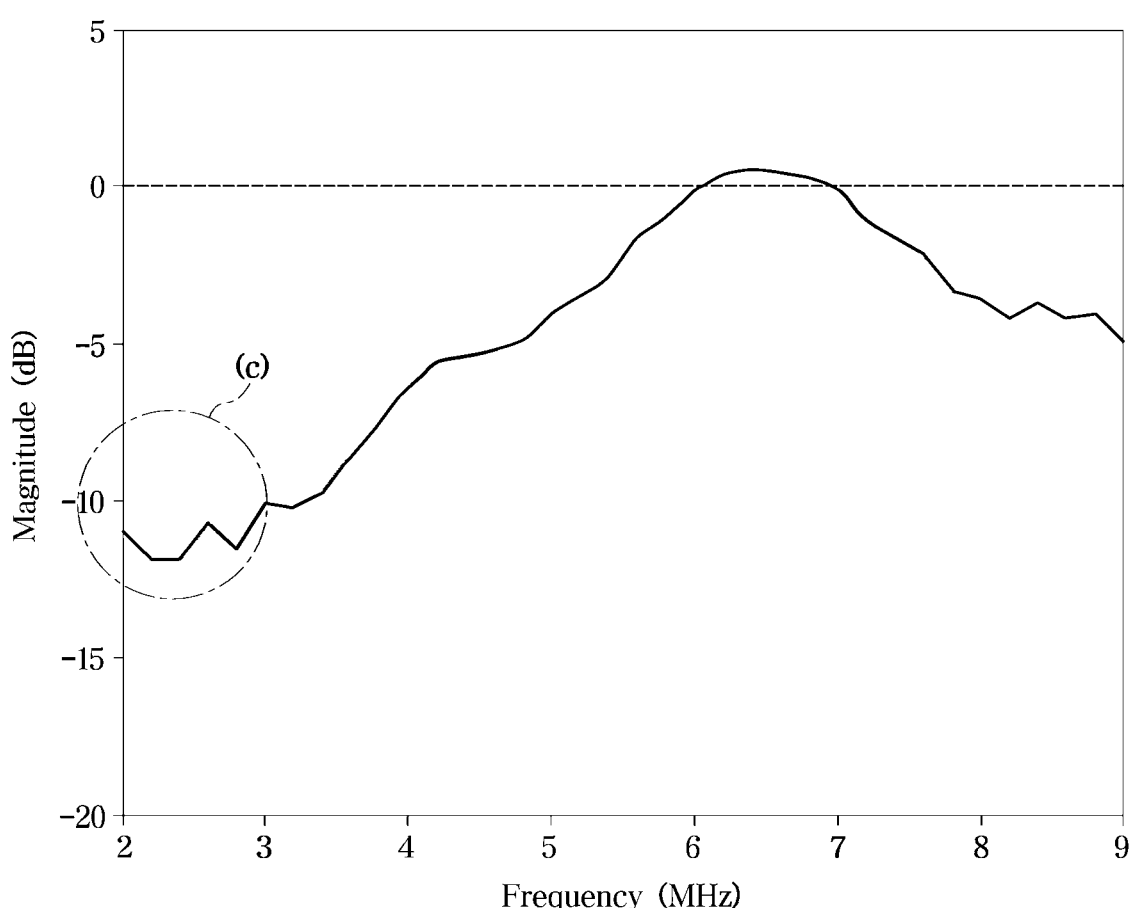
FIG. 6 is a graph related to a sensitivity difference for each frequency band of the element according to an embodiment.

FIG. 6 is a graph related to a sensitivity difference for each frequency band of the element according to an embodiment.

Referring to FIG. 6, the sensitivity of the ultrasonic probe 20 may vary depending on frequency bands of the element 21 before and after the degradation of the element 21. As described above, because the degree of degradation of each of the plurality of elements 21 is different, the frequency characteristics before degradation and the frequency characteristics after degradation may be different.

In FIG. 6, a reference sensitivity (a) before degradation and a sensitivity (b) after the degradation of the element 21 may show the greatest difference in a specific region (c). For example, in the specific region (c), the amplitudes of the element 21 before and after the degradation of the element 21 may be greater than 10 dB.

However, because a difference in amplitudes in regions except for the specific region (c) is within 10 dB and there is a difference in degradation for each frequency band, as illustrated in FIGS. 4 and 5, the quality of an ultrasonic image may be affected.

As illustrated in FIGS. 2 and 3, because the element 21 of the probe 20 is one-dimensional or two-dimensional and a plurality of the elements 21 is provided in one of the transducers, the degree of degradation of each of the elements 21 may vary.

Accordingly, as illustrated in FIGS. 4 to 6, an intensity of a signal varies for each frequency band due to the degradation of each of the plurality of elements 21, so that the shape of a waveform or frequency characteristics of a signal corresponding to a spectrum vary.

Therefore, because the frequency characteristics of the element 21 before degradation may not be maintained when the degradation is compensated for using a method of amplifying the transmission signal as in the prior art, image degradation may be caused. In addition, because the element 21 is already in a degraded state, there is a problem in that the degraded state is further degradative when a higher intensity of the transmission signal is applied.

On the other hand, according to the disclosure, because the reception signal after the degradation of the element 21 may be compensated similarly to the normal frequency characteristics, abnormality of an ultrasonic image may be prevented without getting worse the degraded state of the element 21.

Hereinafter, a detailed method of detecting the degradation of the element 21 by the ultrasonic diagnostic apparatus 1 according to the disclosure, maintaining frequency characteristics before degradation, and compensating for the degradation will be described.

Figure 7A:
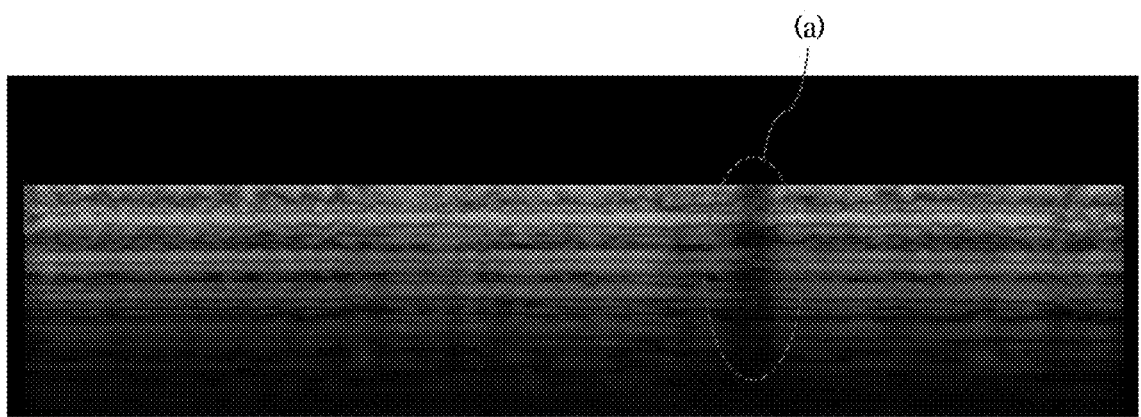
FIGS. 7A and 7B are diagrams for determining degradation of the probe using an in-air image of the ultrasonic diagnostic apparatus according to an embodiment.
Figure 7B:
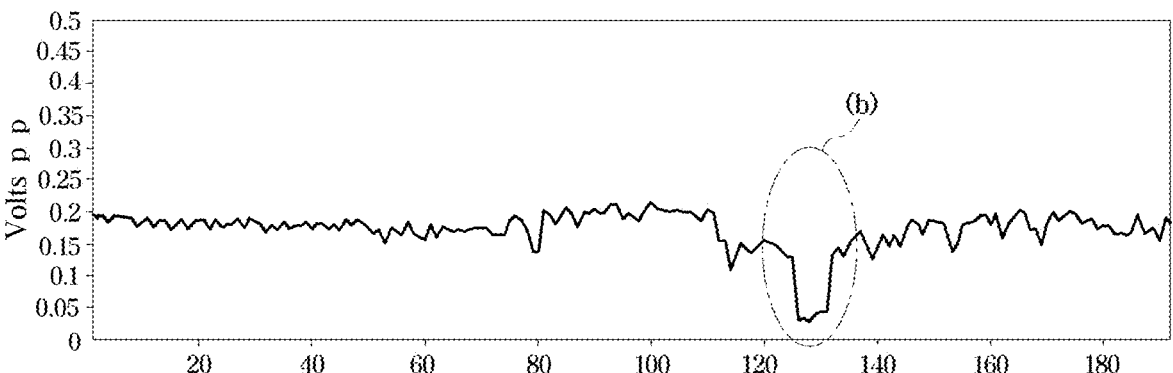

FIGS. 7A and 7B are diagrams for determining degradation of the probe using an in-air image of the ultrasonic diagnostic apparatus according to an embodiment.

Referring to FIGS. 7A and 7B, a processor 185 according to an embodiment may obtain an in-air image by transmitting ultrasonic waves into the air. Specifically, the processor 185 may transmit ultrasonic waves into the air that is not a diagnosis target in order to determine whether the plurality of elements 21 is degradative, and thus may obtain an ultrasonic image as illustrated in FIGS. 7A and 7B.

Referring to FIG. 7A, the processor 185 may control the ultrasonic probe 20 to transmit/receive an ultrasonic signal and obtain an in-air image in the shape of the element 21. In addition, referring to FIG. 7B, the processor 185 may infer the Vpp voltage for each of the elements 21 in the same ultrasonic wave.

Accordingly, as illustrated in FIG. 7B, the processor 185 may determine that the element 21 having a Vpp voltage value lower than or equal to a preset reference value compared to the other elements 21 is degradative.

Specifically, when a sensitivity of a specific one of the elements 21 is determined to be 40% to 75% of an average sensitivity of all of the elements 21, the processor 185 may determine that the specific element 21 is degradative and perform control to compensate for the degradation.

However, when the sensitivity of the specific element 21 is determined to be less than 10% compared to the sensitivity of the element 21 having the highest sensitivity, the processor 185 may determine that the specific element 21 may not be compensated for the degradation and is unusable, and output a message for replacing the element 21 to the display unit 160 instead of control for compensating for the degradation, thereby notifying the user.

In addition, the user may determine whether the element 21 is degradative by visually checking a degradation region (c) in FIG. 7A through the display unit 160 of the ultrasonic diagnostic apparatus 1.

Figure 8:
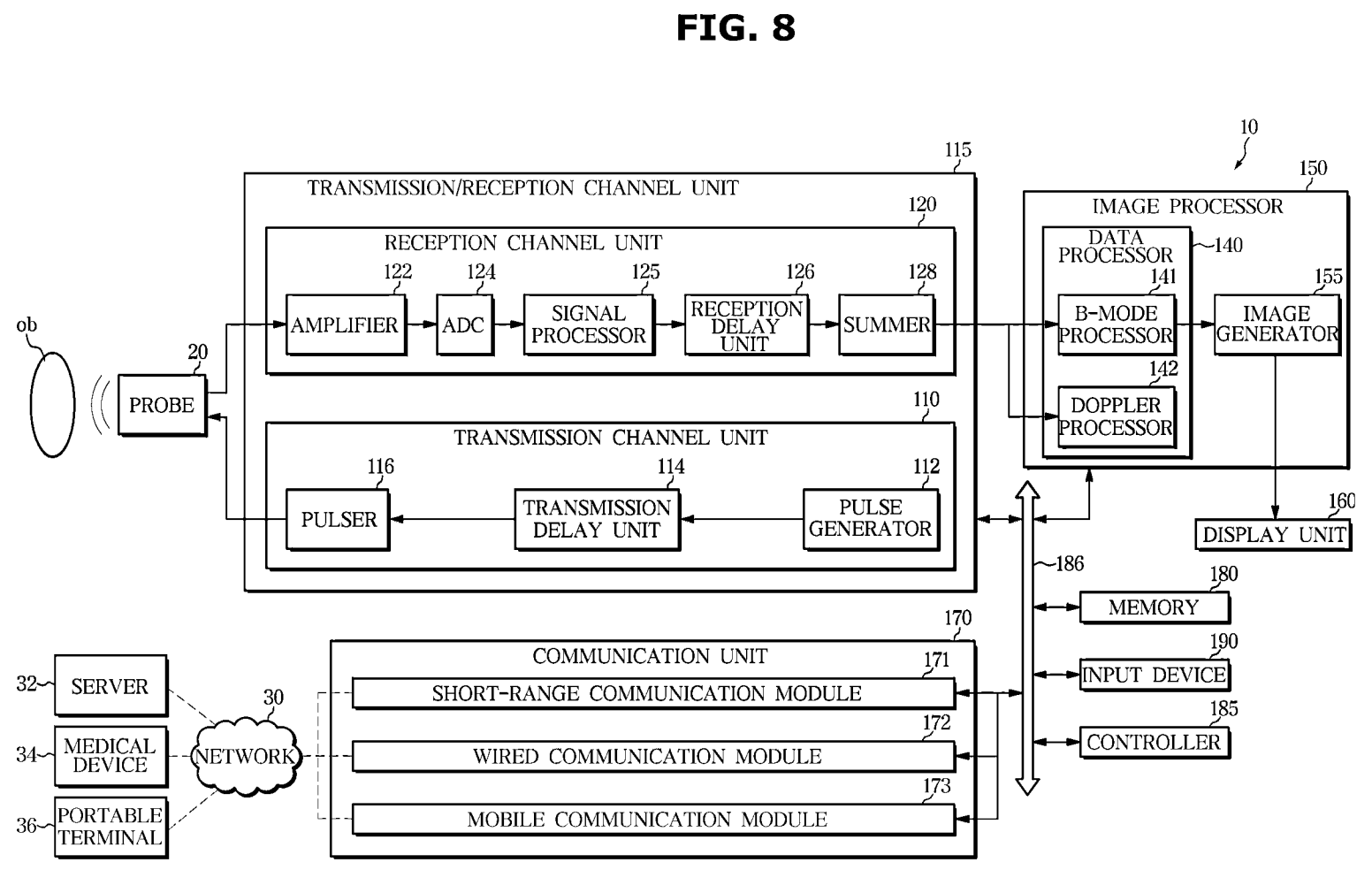

FIG. 8 is a control block diagram of the ultrasonic diagnostic apparatus according to an embodiment.

Referring to FIG. 8, the ultrasonic diagnostic apparatus 1 according to an embodiment may include an ultrasonic transmission/reception channel unit 115, an image processor 150, a communication unit 170, the display unit 160, a memory 180, the input device 190, and a controller, and the components may be connected to each other through a bus 186.

FIG. 8 illustrates that the single probe 20 is connected to the ultrasonic diagnostic apparatus 1, but when an adapter 20 to which a plurality of the probes 20 is fastened is connected thereto, the ultrasonic diagnostic apparatus 1 may include the plurality of probes 20.

The ultrasonic transmission/reception channel unit 115 may include a plurality of transmission channels and a plurality of reception channels.

The probe 20 may transmit an ultrasonic signal (transmission signal) to an object ob depending on a driving signal applied from the ultrasonic transmission/reception channel unit 115, and receive an ultrasonic signal (echo signal) reflected from the object ob.

The probe 20 includes a transducer, and the transducer vibrates depending on an electrical signal transmitted from the ultrasonic diagnostic apparatus 1 and generates ultrasonic waves that is acoustic energy.

The transmission channel unit 110 may include a plurality of transmission channels for supplying the driving signal to the probe 20, and may include a pulse generator 112, a transmission delay unit 114, and a pulser 116. The pulse generator 112 may generate pulses for forming transmission ultrasonic waves according to a predetermined pulse repetition frequency (PRF), and the transmission delay unit 114 may apply a delay time for determining transmission directionality to pulses. Each of the pulses to which the delay time is applied may correspond to each of a plurality of piezoelectric elements included in the probe 20.

That is, the transmission channel unit 110 may include a plurality of transmission channels connected to piezoelectric elements included in the transducer, and may transmit a transmission signal to the piezoelectric elements through each of the transmission channels.

According to various embodiments, each of the plurality of transmission channels may correspond to at least one of the piezoelectric elements. For example, one of the plurality of transmission channels may transmit a transmission signal to one or more of the piezoelectric elements.

The pulser 116, which is a timing corresponding to each pulse to which the delay time is applied, may apply the driving signal (or driving pulse) to the probe 20.

The reception channel unit 120 may include a plurality of reception channels for generating ultrasonic data by processing the ultrasonic signal (echo signal) received from the probe 20, and may include an amplifier 122, an analog digital converter (ADC) 124, a signal processor 125, a reception delay unit 126, and a summer 128. The amplifier 122 amplifies the echo signal for each of the reception channels, and the ADC 124 converts the amplified echo signal from analog to digital.

As will be described later with respect to FIG. 9, the signal processor 125 may determine the degradation of the element 21, select a filter for compensating for a signal transformed by the degradation, transform the signal, and amplify the transformed signal.

The reception delay unit 126 applies the delay time for determining the reception directionality to the digitally converted echo signal, and the summer 128 sums the echo signals processed by the reception delay unit 126, thereby generating ultrasonic data. The reception channel unit 120 may not include the amplifier 122 depending on a type of implementation. That is, when the sensitivity of the probe 20 is improved or the number of bits processed by the ADC 124 is improved, the amplifier 122 may be omitted.

The image processor 150 may generate an ultrasonic image through a scan conversion process for ultrasonic data generated by the ultrasonic transmission/reception channel unit 115.

The ultrasonic image may be a Doppler image representing the moving object ob using a Doppler effect, as well as a gray scale ultrasonic image obtained by scanning the object ob in A mode (amplitude mode), B mode (brightness mode), and M mode (motion mode). The Doppler image may include a blood flow Doppler image (or referred to as a color flow image) showing a flow of blood, a tissue Doppler image a motion of tissue, and a spectral Doppler image showing a moving speed of the object ob as a waveform.

The data processor 140 may process the ultrasonic data.

A B-mode processor 141 extracts and processes a B-mode component from the ultrasonic data. The image generator 155 may generate an ultrasonic image in which an intensity of a signal is expressed as brightness based on the B-mode component extracted by the B-mode processor 141.

Similarly, a Doppler processor 142 may extract a Doppler component from the ultrasonic data, and an image generator 155 may generate a Doppler image (e.g., color flow image) expressing the motion of the object ob in color or waveform based on the extracted Doppler component.

The image generator 155 may generate a three-dimensional ultrasonic image through a volume rendering process for volume data, and may also generate an elasticity image in which a degree of transformation of the object ob due to pressure is imaged.

Furthermore, the image generator 155 may express a variety of additional information as text and graphics on the ultrasonic image. The generated ultrasonic image may be stored in the memory 180.

The ultrasonic image generated through the image generator 155 may be output to the display unit 160.

The communication unit 170 is connected to a network 30 by a wire or wirelessly to communicate with an external device or server. The communication unit 170 may exchange data with a server or other medical devices in a hospital connected through a picture archiving and communication system (PACS). In addition, the communication unit 170 may perform data communication according to a digital imaging and communications in medicine (DICOM) standard.

The communication unit 170 may transmit and receive data related to a diagnosis of the object ob, such as an ultrasonic image, ultrasonic data, and Doppler data of the object ob, through the network 30, and may also transmit and receive medical images captured by other medical devices such as CT, MRI, and X-ray. In addition, the communication unit 170 may receive information about a diagnosis history or treatment schedule of a patient from the server to use the information for the diagnosis of the object ob. Furthermore, the communication unit 170 may perform data communication with a portable terminal of a doctor or patient as well as the server or medical devices in the hospital.

The communication unit 170 may also transmit an ultrasonic image to an external device through the network 30. In this case, when a plurality of ultrasonic images is obtained, each ultrasonic image may be treated as one image and transmitted to the external device.

The communication unit 170 is connected to the network 30 by a wire or wirelessly to exchange data with a server 32, a medical device 34, or a portable terminal 36. The communication unit 170 may include one or more components enabling communication with an external device, and may include, for example, a short-range communication module 171, a wired communication module 172, and a mobile communication module 173.

The short-range communication module 171 refers to a module that performs short-range communication within a predetermined distance. A short-range communication technology according to an embodiment of the disclosure may include wireless LAN, Wi-Fi, Bluetooth, ZigBee, Wi Fi Direct (WFD), ultra-wideband (UWB), infrared data association (IrDA), BLE (Bluetooth Low Energy), near-field communication (NFC), and the like, but the disclosure is limited thereto.

The wired communication module 172 refers to a module that performs communication using an electrical signal or an optical signal, and a wired communication technology according to an embodiment may include a pair cable, a coaxial cable, an optical fiber cable, an Ethernet cable, and the like.

The mobile communication module 173 transmits and receives a wireless signal with at least one of a base station, an external terminal, and a server on a mobile communication network. Herein, the wireless signal may include a voice call signal, a video call signal, or various types of data according to text/multimedia message transmission/reception.

The memory 180 stores a variety of information processed by the ultrasonic diagnostic apparatus 1. For example, the memory 180 may store medical data related to the diagnosis of the object ob, such as input/output ultrasonic data and ultrasonic images, and may also store algorithms or programs to be executed in the ultrasonic diagnostic apparatus 1.

The memory 180 may be implemented as various types of storage media such as the flash memory 180, a hard disk, and an EEPROM. In addition, the ultrasonic diagnostic apparatus 1 may operate a web storage or cloud server that performs a storage function of the memory 180 on a web.

The input device 190 refers to a means for receiving data for a user to control the ultrasonic diagnostic apparatus 1. The input device 190 may include hardware components such as, but not limited to, a keypad, mouse, touchpad, trackball, and jog switch. The input device 190 may also include a fingerprint recognition sensor to recognize a fingerprint of the user. In addition, the input device 190 may further include various components such as an electrocardiogram measurement module, a respiration measurement module, a voice recognition sensor, a gesture recognition sensor, an iris recognition sensor, a depth sensor, and a distance sensor. In particular, a touch screen in which the touch pad forms a mutual layer structure with the display unit 160 described above may also be included.

In this case, the ultrasonic diagnostic apparatus 1 according to an embodiment of the disclosure may display an ultrasonic image of a predetermined mode and a control panel for the ultrasonic image on the touch screen. Also, the ultrasonic diagnostic apparatus 1 may detect a touch gesture of the user for the ultrasonic image through the touch screen.

The ultrasonic diagnostic apparatus 1 according to an embodiment of the disclosure may physically include some buttons frequently used by the user among buttons included in a control panel of a general ultrasonic diagnostic apparatus, and may provide the remaining buttons through the touch screen in the form of a graphical user interface (GUI).

The controller controls the overall operation of ultrasonic diagnostic apparatus 1. That is, the controller may control operations between the probe 20, the ultrasonic transmission/reception channel unit 115, the image processor 150, the communication unit 170, the memory 180, and the input device 190, which illustrate in FIG. 8.

The controller may include the at least one memory 180 in which a program performing operations, which will be described later, is stored and the at least one processor 185 executing the stored program. The ultrasonic transmission/reception channel unit 115, the image processor 150, and the controller may separately use the memory 180 and the processor 185, or share the memory 180 and the processor 185.

Specifically, the processor 185 may modulate an echo signal based on comparison between frequency characteristic data of the echo signal and pre-stored normal frequency characteristic data.

Also, the processor 185 may amplify the modulated echo signal and transmit the amplified signal to the reception delay unit.

Some or all of the probe 20, the ultrasonic transmission/reception channel unit 115, the image processor 150, the display unit 160, the communication unit 170, the memory 180, the input device 190, and the controller may be operated by software modules, but the disclosure is not limited thereto, and some of the above components may be operated by hardware modules. In addition, at least some of the ultrasonic transmission/reception channel unit 115, the image processor 150, and the communication unit 170 may be included in the controller, but the disclosure is not limited to such an implementation form.

The probe 20 connected to a slot 195 transmits identification information (e.g., identification number information, type information of the probe 20, etc.) of the probe 20 to the ultrasonic diagnostic apparatus 1 through a cable, and the ultrasonic diagnostic apparatus 1 provides a user interface for selecting the probe 20 on the display unit 160 based on the identification information of the probe 20. Accordingly, an operator may select the probe 20 the operator wants to use through the user interface, and an image generated based on the ultrasonic signal obtained from the selected probe 20 is output to the display unit 160.

Hereinafter, the signal processor compensating for signal transformation due to the degradation of the element 21 between the ADC and the reception delay unit will be described in detail.

Figure 9:
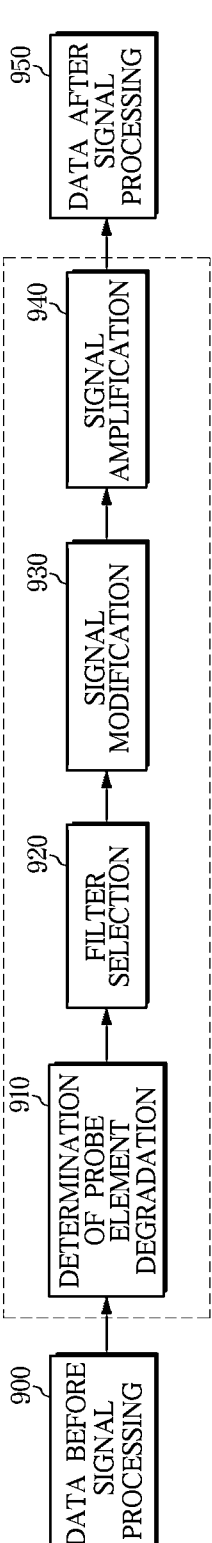
FIG. 9 is a block diagram illustrating a signal processor of the ultrasonic diagnostic apparatus according to an embodiment.

FIG. 9 is a block diagram illustrating a signal processor of the ultrasonic diagnostic apparatus according to an embodiment.

Referring to FIG. 9, the processor 185 may receive data before signal processing through the element 21 (900). Thereafter, the processor 185 may determine whether the element 21 of the probe 20 is degradative (910), and as described above with reference to FIGS. 7A and 7B, the degradation may be determined by the Vpp voltage value of the element 21 inferred from the in-air image by the processor 185 or by eyes of the user.

When it is determined that the element 21 of the probe 20 is degradative, the processor 185 may select a filter to make a frequency characteristic variation for each frequency band equal (920). In this case, the filter may include a band stop filter consisting of a low pass filter and a high pass filter.

The processor 185 may transform a signal to be similar to normal frequency characteristics before the degradation of the element 21 by applying the band stop filter to the signal received from the degradative element 21 (930). In this case, the processor 185 may transform the signal with a method of reducing a signal of a frequency band having the smallest difference between before and after degradation based on a frequency band having the largest difference between before and after degradation.

Thereafter, the processor 185 may amplify the transformed signal similarly to the normal frequency characteristics before degradation (940), and may transmit data after signal processing, which is an amplified signal, to the reception delay unit (950).

Figure 10:
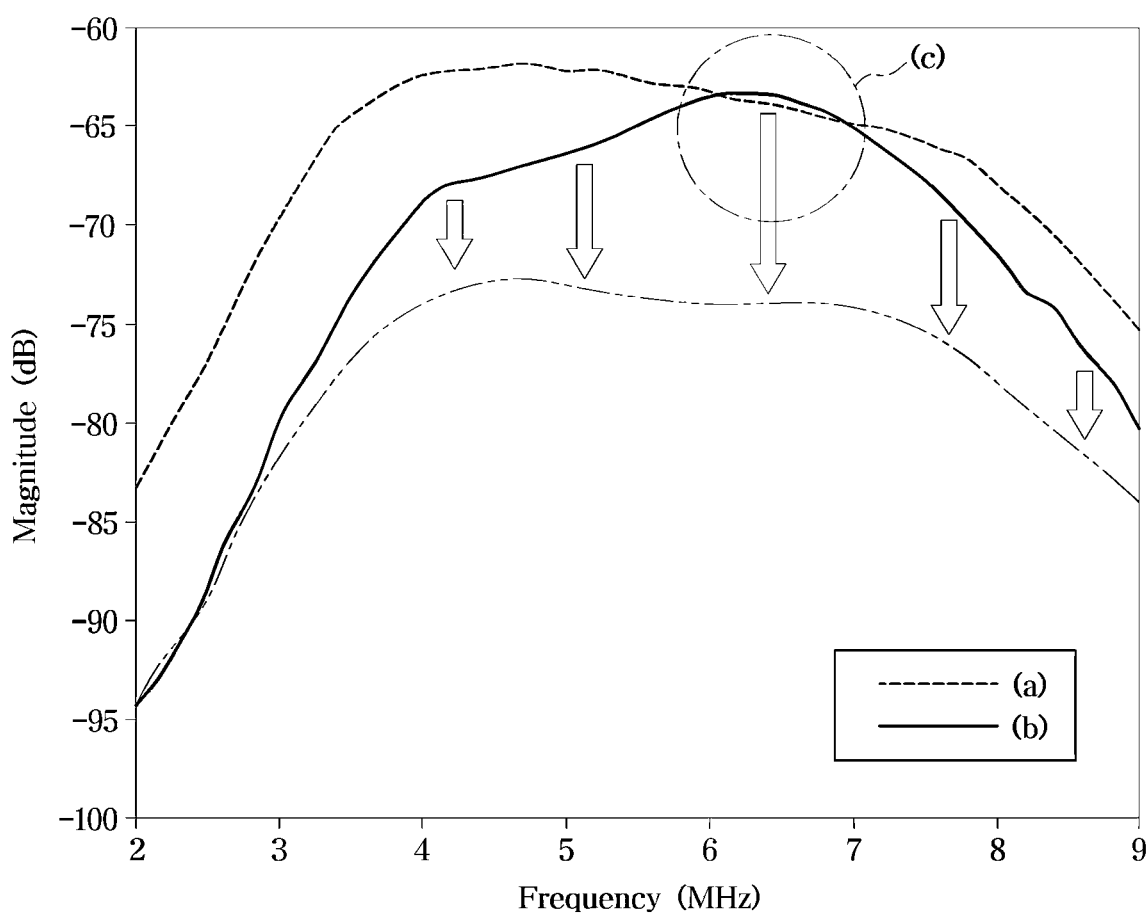
FIG. 10 is a graph illustrating that a processor according to an embodiment processes a signal such that frequency characteristics after the degradation of the element are similar to those before degradation.

FIG. 10 is a graph illustrating that the processor 185 according to an embodiment processes a signal such that frequency characteristics after the degradation of the element 21 are similar to those before degradation.

Referring to FIG. 10, the processor 185 may compare the frequency characteristic data of the echo signal with the pre-stored normal frequency characteristic data in order for the element 21 to maintain the frequency characteristics before degradation.

Specifically, a frequency characteristic graph (a) before degradation and a frequency characteristic graph (b) after degradation may have different amplitude variations for each frequency band. Accordingly, the frequency characteristics before degradation may not be maintained simply by simply amplifying the signal received from the degradative element 21. Therefore, the processor 185 may determine a frequency band having a maximum amplitude difference in the same frequency band by comparing amplitudes of the frequency characteristics before degradation and the frequency characteristics after degradation.

Thereafter, the processor 185 may modulate the echo signal to have the same amplitude variation by reducing amplitudes in the remaining frequency bands based on an amplitude difference value in the frequency band having the maximum amplitude difference.

That is, the processor 185 may change the amplitude the most in a region (c) in which the difference in the amplitudes is the smallest to modulate the echo signal so that the echo signal after the degradation of the element 21 has a predetermined amplitude difference from the echo signal before the degradation of the element 21 in all of the frequency bands.

Accordingly, the processor 185 may modulate the echo signal so that the frequency characteristics after degradation are the same as the frequency characteristics before degradation.

A method of reducing the amplitudes in the remaining frequency bands based on the amplitude difference value in the frequency band having the maximum amplitude difference by the processor 185 will be specifically described with reference to FIG. 11.

Figure 11:
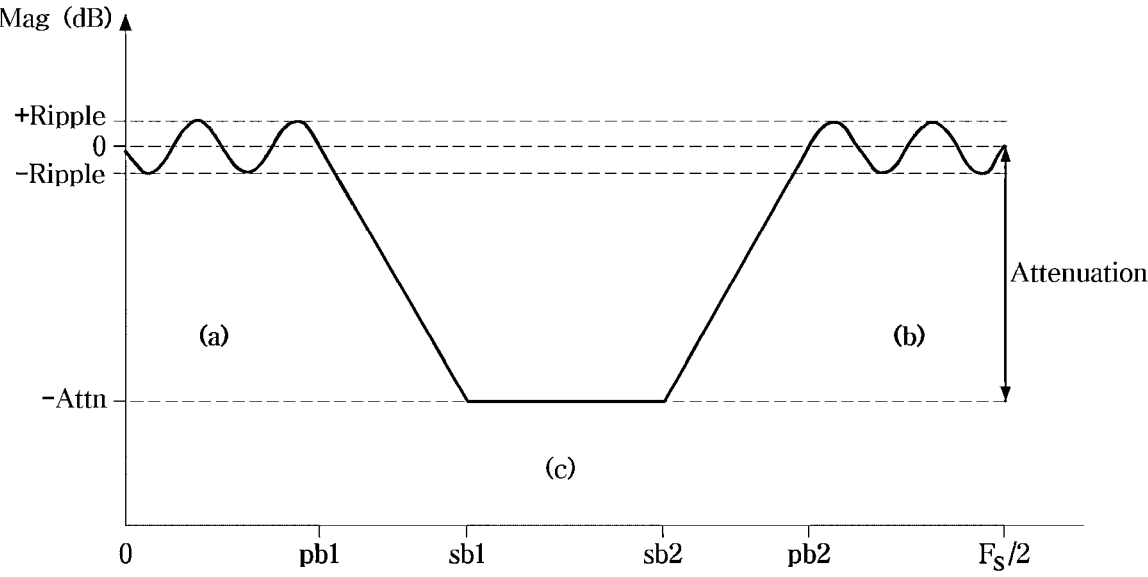
FIG. 11 is a graph related to a band stop filter applied to the ultrasonic diagnostic apparatus according to an embodiment.

FIG. 11 is a graph related to a band stop filter applied to the ultrasonic diagnostic apparatus 1 according to an embodiment.

The band stop filter may refer to a filter that blocks signals in a frequency band between two specific cutoff frequencies and the frequencies and passes other frequencies without attenuation. The band stop filter may consist of the low pass filter and the high pass filter.

Referring to FIG. 11, the processor 185 may determine a frequency band between sb1 and sb2, which are two cutoff frequencies, as a stop band c, and may determine other frequency bands below pb1 and above pb2 as pass bands a and b, respectively.

Accordingly, the processor 185 may apply the band stop filter to a frequency band having a small amplitude difference based on a frequency band having the largest difference in the amplitudes to modulate the echo signal so that the spectrums and frequency characteristics before degradation are maintained.

However, a filter applied to the ultrasonic diagnostic apparatus 1 according to an embodiment is not limited to the band stop filter, and various filters stored in the memory 180 in the form of a look-up table and suitable for the characteristics of the probe 20 may be included.

The processor 185 may also transform the echo signal by selecting one of frequency filters stored in the form of a lookup table based on an artificial intelligence model learned through machine learning.

Figure 12:
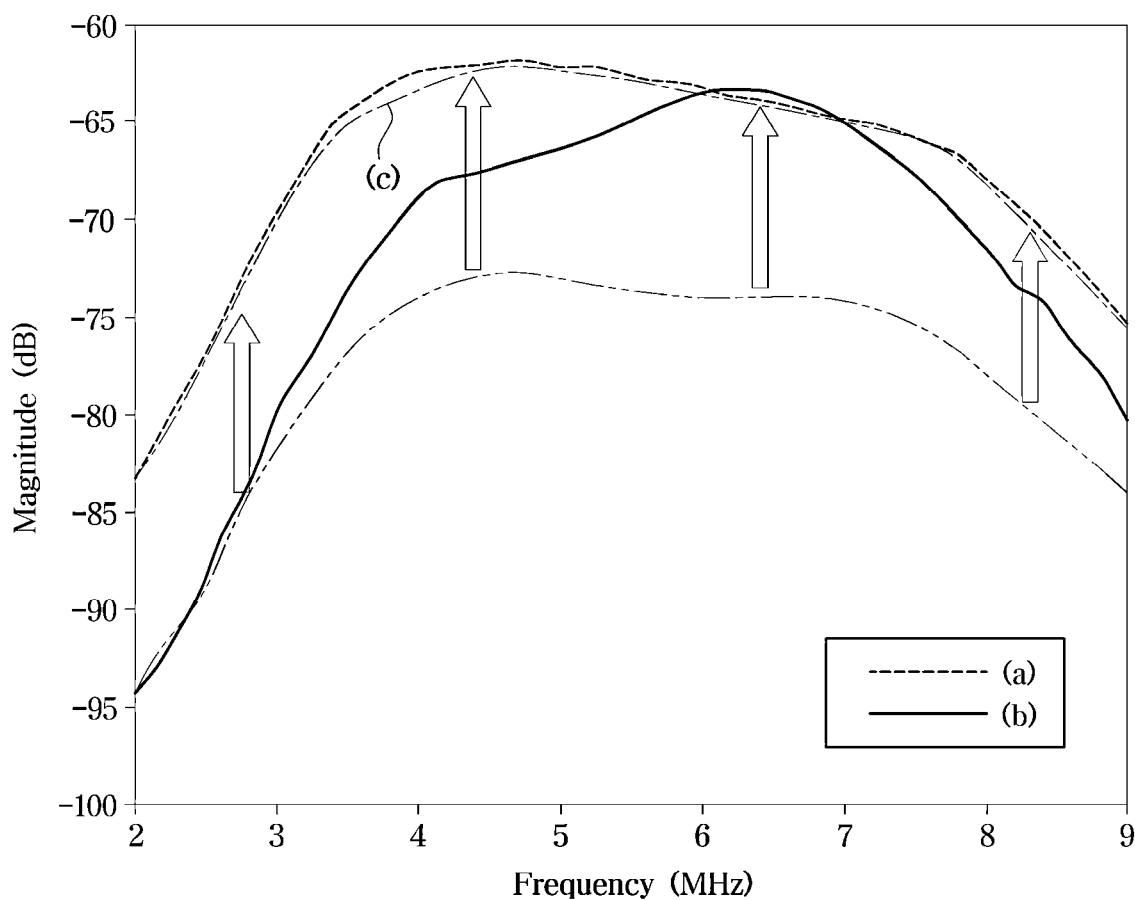
FIG. 12 is a graph related to amplifying a transformed signal by the processor according to an embodiment.

FIG. 12 is a graph related to amplifying a transformed signal by the processor 185 according to an embodiment.

As illustrated in FIG. 12, the processor 185 may modulate the echo signal after the degradation of the element 21 to maintain the frequency characteristics of the element 21 before degradation, and then amplify the echo signal.

Specifically, the processor 185 may amplify the modulated echo signal so that a difference in the amplitudes of the frequency characteristic data of the modulated echo signal and the normal frequency characteristic data in the same frequency band decreases to a preset threshold value or less.

As described above, the processor 185 may modulate a signal by modulating a signal of a frequency characteristic graph (b) after degradation so that the echo signal after the degradation of the element 21 has a constant amplitude difference from the echo signal before the degradation of the element 21 in all of the frequency bands.

That is, the processor 185 may generate a compensated frequency characteristic graph (c) by modulating the echo signal so that a difference between a frequency characteristic graph (a) and the amplitude before degradation decreases to the preset threshold value or less.

Because the compensated frequency characteristic graph (c) maintains the frequency characteristic graph (a) before degradation and the frequency characteristic thereof and the magnitude of the signal also equals to or less than the threshold value as in the frequency characteristic graph (a) before degradation, the quality of the ultrasonic image may be maintained similarly even after degradation.

That is, because the ultrasonic diagnostic apparatus 1 according to an embodiment compensates for degradation by using a method of modulating a reception signal rather than a method of amplifying a transmission signal, the frequency characteristics before the degradation of the element 21 may be maintained. Accordingly, degradation in the quality of the ultrasonic image may be prevented, and because the magnitude of the transmission signal is not applied higher, there is an effect that the degradation state is not further degraded.

Figure 13:
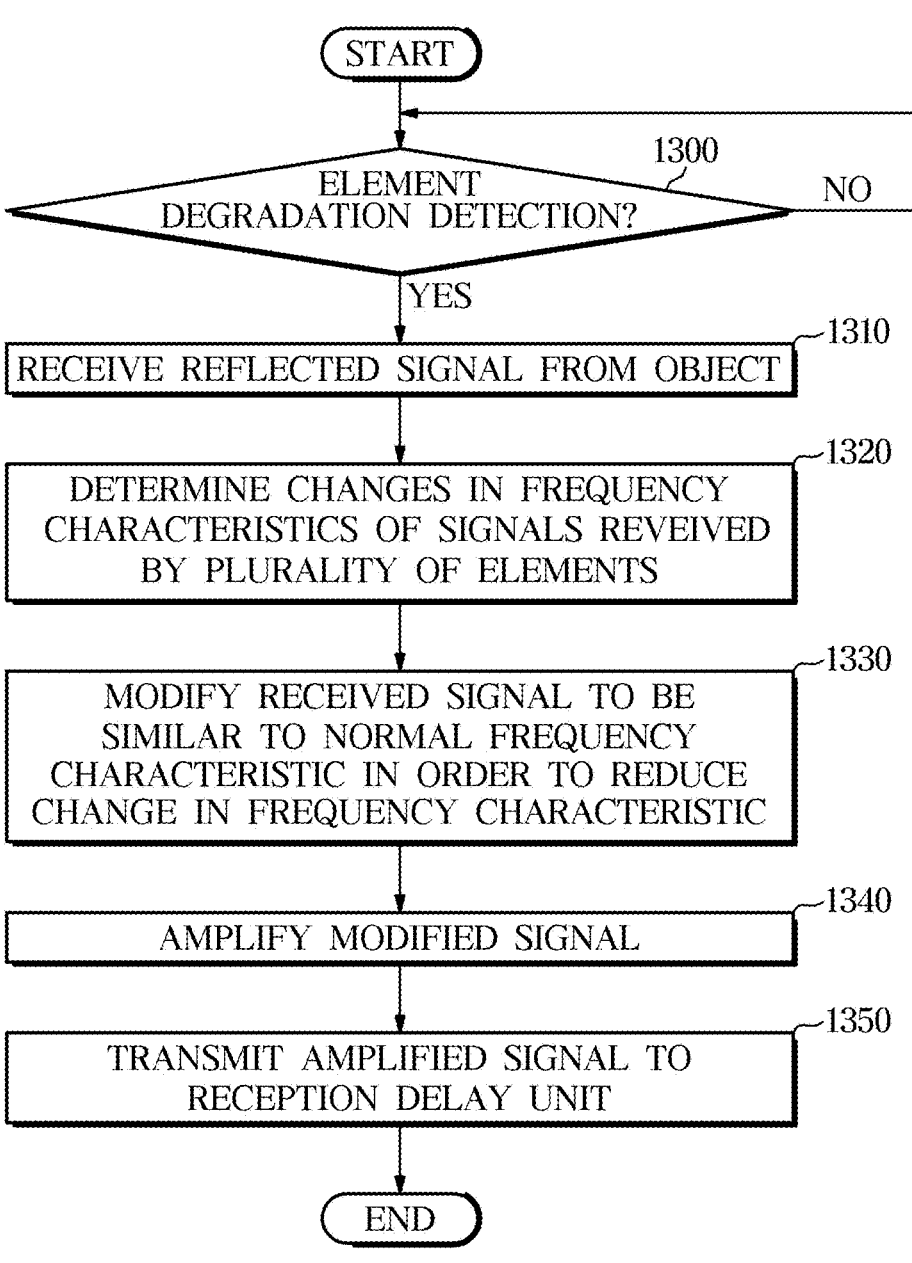
FIG. 13 is a control flowchart of a control method of the ultrasonic diagnostic apparatus according to an embodiment.

FIG. 13 is a control flowchart of a control method of the ultrasonic diagnostic apparatus 1 according to an embodiment.

Referring to FIG. 13, the processor 185 may detect the degradation of the element 21 of the probe 20 (1300). However, because the user may directly check the degradation of the element 21 of the probe 20 through the in-air image, when the user detects the degradation of the element 21, the processor 185 may also receive a signal by operating a degradation compensation function.

When the degradation of the element 21 of the probe 20 is detected (YES in 1300), the processor 185 may receive an echo signal that is a reflected signal from an object (1310).

Thereafter, the processor 185 may determine changes in frequency characteristics of signals received from the plurality of elements 21 (1320).

The processor 185 may determine a change in frequency characteristics by comparing the frequency characteristic data of the echo signal with the pre-stored normal frequency characteristic data, and the normal frequency characteristic data may include normal pulse echo data obtained through the element 21 in a test process after manufacturing.

Specifically, the processor 185 obtains information on the Vpp voltage, frequency bandwidth, and spectral size for each frequency band by analyzing pulse echo data for all of the elements 21 and may obtain an average value, a median value, or a maximum value, which are representative characteristic values, and the normal pulse echo data may include the representative characteristic values.

The processor 185 of the ultrasonic diagnostic apparatus 1 according to an embodiment may determine a change in frequency characteristics by comparing the pulse echo data obtained through the plurality of elements 21 with the normal pulse echo data.

That is, the processor 185 may compare the pulse echo data, which is data obtained by putting the degradative probe 20 into a liquid and transmitting and receiving ultrasonic waves, with the normal pulse echo data obtained in a normal state before degradation.

The processor 185 may determine the difference in the amplitudes in the same frequency band as a frequency characteristic variation by comparing the pulse echo data obtained through the plurality of elements 21 with the normal pulse echo data.

The processor 185 of the ultrasonic diagnostic apparatus 1 according to another embodiment may determine a change in frequency characteristics by comparing the in-air image data obtained through the plurality of elements 21 with the normal pulse echo data including the representative characteristic values.

That is, the processor 185 may compare the in-air image data, which is data obtained by transmitting and receiving ultrasonic waves to and from the degradative probe 20 in the air, with the normal pulse echo data obtained in the normal state before degradation.

The processor 185 may determine the difference in the amplitudes in the same frequency band as a frequency characteristic variation by comparing the in-air image data obtained through the plurality of elements 21 with the normal pulse echo data.

The processor 185 of the ultrasonic diagnostic apparatus 1 according to another embodiment may obtain element 21 inspection data based on receiving a user input for inspecting the plurality of elements 21. Thereafter, the processor 185 may determine a change in the frequency characteristic by comparing the element 21 inspection data with the normal pulse echo data including the representative characteristic values.

That is, the user may compare the in-air image data, which is data obtained by transmitting and receiving ultrasonic waves to and from the degradative probe 20 in the test air, with the normal pulse echo data obtained in the normal state before degradation.

The processor 185 may determine the difference in the amplitudes in the same frequency band as the frequency characteristic variation by comparing the in-air image data obtained through the plurality of elements 21 with the normal pulse echo data.

Thereafter, the processor 185 may correct the received signal to be similar to the normal frequency characteristic before degradation in order to reduce the change in the determined frequency characteristic (1330).

That is, as described above, the processor 185 may modulate and correct the echo signal so that the echo signal after the degradation of the element 21 has the constant amplitude difference from the echo signal before the degradation of the element 21 in all of the frequency bands.

The processor 185 may amplify the corrected signal so that an amplitude of the signal and an amplitude of a signal before degradation in the same frequency band are equal to or less than a preset threshold value (1340), and the processor 185 may transmit the amplified signal to the reception delay unit (1350).

According to the ultrasonic diagnostic apparatus 1 according to an embodiment, because only the reception signal is modulated, time and cost losses in which the transmission signal is changed according to the characteristics of the probe 20 and then the characteristics of the reception signal are checked again may be reduced.

In addition, because the processor 185 maintains the existing frequency and sensitivity characteristics even when the element 21 is degradative while checking the state of the element 21 in real time, degradation of image quality may be prevented.

As is apparent from the above, according to an aspect of the disclosure, by determining whether an element has degradative, frequency and sensitivity characteristics of the element can be maintained similar to those before degradation, and thus the degradation in quality of an ultrasonic image can be prevented.

According to an aspect of the disclosure, because an ultrasonic transmission signal is maintained and only a reception signal is compensated, it is not necessary to double-check characteristics of the reception signal after transmission signal is changed by reflecting characteristics of a probe, which can increase efficiency.

The disclosed embodiments may be implemented in the form of a recording medium storing instructions executable by a computer. The instructions may be stored in the form of program code, and when executed by the processor 185, a program module may be created to perform the operations of the disclosed embodiments. The recording medium may be implemented as a computer-readable recording medium.

The computer-readable recording medium includes any type of recording medium in which instructions readable by the computer are stored. For example, the recording medium may include a read only memory (ROM), a random access memory (RAM), a magnetic tape, a magnetic disk, a flash memory, an optical data storage device, and the like.

Also, the computer-readable recording medium may be provided in the form of a non-transitory storage medium. Herein, the 'non-transitory storage medium' only means that it is a tangible device and does not contain a signal (e.g., electromagnetic wave), and this term does not distinguish between a case where data is semi-permanently stored in a storage medium and a case where data is temporarily stored. For example, the 'non-transitory storage medium' may include a buffer in which data is temporarily stored.

According to an embodiment, methods according to various embodiments of the disclosure may be included and provided in a computer program product. The computer program product may be traded between a seller and a buyer as a commodity. The computer program product may be distributed in the form of a device-readable recording medium (e.g., compact disc read only memory (CD-ROM)), or may be distributed (e.g., downloaded or uploaded) online, through an application store (e.g., Play Store™) or directly between two user devices (e.g., smartphones). In the case of online distribution, at least a part of the computer program product (e.g., a downloadable app) may be temporarily stored or temporarily created in the device-readable recording medium such as a server of a manufacturer, a server of an application store, and a memory of a relay server.

The above detailed description is illustrative of the disclosure. Also, the contents described above are intended to illustrate and describe preferred embodiments of the disclosure, and the disclosure may be used in various other combinations, modifications, and environments. That is, the contents described above may be changed or modified within the scope of the concept of the invention disclosed in this specification, within the scope equivalent to the written disclosure and/or within the scope of skill or knowledge in the art. The above embodiments describe the best state for implementing the technical idea of the disclosure, and various changes of the above embodiments required in specific application fields and uses of the disclosure are also possible. Therefore, the detailed description herein is not intended to limit the disclosure to the disclosed embodiments. Also, the appended claims should be construed to cover other embodiments as well.

What is claimed is:

1. An ultrasonic diagnostic apparatus comprising:
a probe comprising a plurality of elements provided to transmit an ultrasonic signal to an object and receive an echo signal reflected from the object; and
at least one processor configured to:
determine degradation of the echo signal obtained through the plurality of elements,
modify the echo signal based on comparing frequency characteristic data of the echo signal with pre-stored normal frequency characteristic data and amplify the modified echo signal,
compare amplitude of the frequency characteristic data of the echo signal with amplitude of the normal frequency characteristic data in the same frequency band,
determine a frequency band having a maximum difference of amplitudes among the frequency bands,
modify the echo signal by applying frequency filters so that the difference of the amplitudes in the same frequency band is equal to the difference in the amplitudes in the determined frequency band in which the difference in the amplitudes is maximum,
amplify the modified echo signal so that the difference in the amplitudes of the frequency characteristic data of the modified echo signal and the normal frequency characteristic data in the same frequency band decreases to a preset threshold value or less, and
transmit the amplified echo signal.

2. The ultrasonic diagnostic apparatus according to claim 1, wherein
the at least one processor is configured to modify the echo signal by selecting one of the frequency filters stored in the form of a look-up table.

3. The ultrasonic diagnostic apparatus according to claim 1, wherein
the normal frequency characteristic data comprises normal pulse echo data of the elements.

4. The ultrasonic diagnostic apparatus according to claim 3, wherein
the at least one processor is configured to modify the echo signal by comparing pulse echo data obtained through the plurality of elements with the normal pulse echo data.

5. The ultrasonic diagnostic apparatus according to claim 3, wherein
the at least one processor is configured to modify the echo signal by comparing in-air image data obtained through the plurality of elements with the normal pulse echo data.

6. The ultrasonic diagnostic apparatus according to claim 3, wherein
the at least one processor is configured to obtain element inspection data based on receiving a user input for inspecting the plurality of elements, and modify the echo signal by comparing the element inspection data with the normal pulse echo data.

7. A control method of an ultrasonic diagnostic apparatus comprising a plurality of elements provided to transmit an ultrasonic signal to an object and receive an echo signal reflected from the object and a probe, wherein the control method comprises:
Determining a degradation of the echo signal obtained through the plurality of elements,
modifying the echo signal based on comparing frequency characteristic data of the echo signal with pre-stored normal frequency characteristic data;
amplifying the modified echo signal; and
transmitting the amplified echo signal,
wherein the modifying the echo signal comprises:
comparing amplitude of the frequency characteristic data of the echo signal with amplitude of the normal frequency characteristic data in the same frequency band;
determining a frequency band having a maximum difference in amplitudes among the frequency bands; and
modifying the echo signal by applying frequency filters so that the difference in the amplitudes in the same frequency band is equal to the difference in the amplitudes in the determined frequency band in which the difference in the amplitudes is maximum; and
wherein the amplifying the modified echo signal comprises amplifying the modified echo signal so that the difference in the amplitudes of the frequency characteristic data of the modified echo signal and the normal frequency characteristic data in the same frequency band decreases to a preset threshold value or less.

8. The control method according to claim 7, wherein
the modifying of the echo signal comprises modifying the echo signal by selecting one of the frequency filters stored in the form of a look-up table.

9. The control method according to claim 7, wherein
the normal frequency characteristic data comprises normal pulse echo data of the elements.

10. The control method according to claim 9, wherein
the modifying of the echo signal comprises modifying the echo signal by comparing pulse echo data obtained through the plurality of elements with the normal pulse echo data.

11. The control method according to claim 9, wherein the modifying of the echo signal comprises modifying the echo signal by comparing in-air image data obtained through the plurality of elements with the normal pulse echo data.

12. The control method according to claim 9, wherein the modifying of the echo signal comprises: obtaining element inspection data based on receiving a user input for inspecting the plurality of elements; and modifying the echo signal by comparing the element inspection data with the normal pulse echo data.

\* \* \* \* \*